United States Patent [19]
Korenstein et al.

[11] Patent Number: 5,964,726
[45] Date of Patent: Oct. 12, 1999

[54] APPARATUS AND METHOD FOR EFFICIENT INCORPORATION OF MOLECULES INTO CELLS

[75] Inventors: Rafi Korenstein, Rehovot; Yosef Rosemberg, Ra'Anana, both of Israel

[73] Assignee: RAMOT University Authority for Applied Research and Industrial Development, Tel-Aviv, Israel

[21] Appl. No.: 08/834,340

[22] Filed: Apr. 16, 1997

Related U.S. Application Data

[63] Continuation of application No. 08/394,696, Feb. 24, 1995, abandoned.

[30] Foreign Application Priority Data

Feb. 25, 1994 [IL] Israel ........................................ 108775

[51] Int. Cl.⁶ .................................................... A61N 1/30
[52] U.S. Cl. ......................... 604/20; 604/21; 435/173.4; 435/173.5; 935/52
[58] Field of Search ................................ 604/20–21, 49; 435/173–1, 173.6; 935/52–58; 128/641

[56] References Cited

U.S. PATENT DOCUMENTS

| | | | |
|---|---|---|---|
| 4,441,972 | 4/1984 | Pohl | 204/180 R |
| 4,476,004 | 10/1984 | Pohl | 204/299 R |
| 4,578,168 | 3/1986 | Hofmann | 204/299 R |
| 4,663,292 | 5/1987 | Wong et al. | 435/287 |
| 5,019,034 | 5/1991 | Weaver et al. | 604/20 |
| 5,124,259 | 6/1992 | Tada | 935/52 |
| 5,304,486 | 4/1994 | Chang | 435/173.5 |
| 5,371,003 | 12/1994 | Murry et al. | 435/173.5 |
| 5,389,069 | 2/1995 | Weaver | 604/21 |
| 5,439,440 | 8/1995 | Hofmann | 604/20 |
| 5,674,267 | 10/1997 | Mir et al. | |
| 5,702,359 | 12/1997 | Hofmann et al. | |

OTHER PUBLICATIONS

Kim et al. "Electroporation of extraneous proteins into CHO cells: increased efficacy by utilizing centrifugal . . . " *Experimental Cell Research*, 197:207–212 (1991).

Tatham and Lindau, *J. Gen. Physiol.* 95(3) :459–76 (1990).

*Primary Examiner*—Mark Bockelman
*Attorney, Agent, or Firm*—Kohn & Associates

[57] ABSTRACT

A method and apparatus (20) for introducing molecules and macromolecules into a membrane vesicle, a cell or a tissue by (a) applying a train of low unipolar or alternating voltage pulses to molecules/macromolecules and cells, (b) increase the concentration of the molecules/macromolecules at the surface of the cells, leading to an increased interaction of the molecules/macromolecules with the membrane of the cell while also causing electrophoretic movement of charged proteins and lipids in the cell membrane, and (c) causing the destabilization of the cell membrane whereby the molecules/macromolecules penetrate into the cytosol via an endocytic process and via diffusion through structural defects in the membrane lipid bilayer.

The apparatus (20) includes a support plate (36) having apertures (38) for allowing electrodes (22) to pass therethrough. Support tubes (34) located within the apertures (38) slideably surround the electrodes (22). An electric current supplying mechanism (32) connected to the electrodes (22) supplies sufficient electrical current to a cell for facilitating the introduction of molecules or macromolecules into the cell.

5 Claims, 10 Drawing Sheets

5,964,726

APPARATUS AND METHOD FOR EFFICIENT INCORPORATION OF MOLECULES INTO CELLS

This is a continuation of application Ser. No. 08/394,696 filed on Feb. 24, 1995 now abandoned.

TECHNICAL FIELD

This invention relates to a system for transferring molecules into cells and, more particularly, to a pulsed low voltage system capable of macromolecular transfer.

BACKGROUND OF THE INVENTION

In order to introduce molecules into cells, the permeability barrier of the cell membrane must be overcome. Present day research has created two categories of approach for loading cells with otherwise membrane impermeable molecules.

In a first method, low molecular weight molecules are incorporated into cells based either on the employment of lipophilic molecules which are modified into hydrophilic molecules following their penetration into the cytosol by intracellular enzymes, such esterases which act on, in example, the pH indicator 2', 7'-bis(2-carboxyethyl) -5(6)-carboxyfluorescein, acetoxy methyl ester or by adenosine tri-phosphate induced formation of small pores in the membrane.

The second method relates to the incorporation of high molecular weight molecules and is based on several approaches. One approach is the use of chemicals such as detergents, polyethyleneglycol, and lipofectin. Additional approaches include liposome-cell fusion, electroporation, and cell bombardment by coated molecules.

A problem with these methods is that they are either destructive of cells or the methods are inefficient and are of restricted commercial use.

An application requiring the introduction of molecules into cells is the field of gene therapy. In this application, macromolecules, generally DNA, must be introduced into the cell. The cells must be transfected with the DNA leading to transformed viable cells.

While significant progress has been made in manipulating cellular genes, the application to gene therapy has been limited and the field of gene therapy is still not commercially developed. One major limiting factor to apply gene therapy effectively is the need to achieve a very high number of transformed cells. In most cases following transfection, transformation does not occur and neither further selection nor multiplication of cells can be achieved. Thus, the efficiency of transfection resulting in transformation is the rate limiting step for applications of gene therapy.

One successful approach in gene therapy has been to use a gene spliced into a retrovirus as a vector to introduce the gene into the target cell. However, the disadvantage of this strategy is that it involves the multiplication of target cells in vitro. Other limitations of this approach are the limited size of the gene that can be carried by the vector and be implanted and the procedures needed to express only the target gene without the additional expression of the viral genes. This procedure is limited to DNA and does not accommodate other molecular species that could, for example, lead to the intracellular employment of exogenous enzymes, such as restriction enzymes, for gene manipulations.

Fusing liposomes is another approach. The liposomes are loaded with the appropriate genes and are fused with the target cells.

An alternative procedure for the introduction of genes into cells is based on exposing the cells to exogenous DNA in high electric fields, the procedure being known as electroporation. Electroporation can be generally defined as formation of hydrophilic pores through an electrical process where larger pores allow higher permeability. Electroporation utilizes short, high voltage electrical pulses to produce a transient high permeability state (reversible electrical breakdown, REB) which occurs at the beginning of the high permeability state. REB is a decrease in the electrical resistance of a tissue which is caused by brief exposure to an abnormally high transtissue potential.

U.S. Pat. No. 5,019,034 to Weaver discloses the use of a high voltage, short duration electrical pulse on the tissue surface to produce electroporation of molecules into cells of the tissue.

However, these existing methods suffer from at least one of the following problems:

(1) There is a low efficiency of loading or transfection of high molecular weight molecules (i.e., macromolecules).

(2) The demonstrated loading of macromolecules appears limited to DNA. There is a lack of loading of high molecular weight proteins, enzymes of the molecular weight of 250 kD and higher, as disclosed in the literature.

(3) Many of the extensively used methods involve steps for transfection that have a high rate of cell killings.

The present invention provides an alternative method to the above, which not only enables the incorporation into cells of macromolecules without destruction of the cells, but also provides an efficient introduction of the molecules. The method can be accomplished in vivo or in vitro.

Several prior art electrodes have been used for incorporating molecules into adherent cells (cells growing attached to a surface). One such electrode was based on causing cells to adhere to a first electrode surface and then applying a second electrode on top of the cells adhered to the first. A second prior art electrode was based upon the application of several sets of parallel electrodes which were positioned perpendicular to the surface to which the cells were adhered. The second electrode configuration required electrode-cell contact which created the problem that because the cells were of such small size, in order to insure that the cells were in contact with the two electrodes, the electrodes had to be built to precise tolerances which were difficult to obtain.

The present invention provides an alternative electrode to the above, which not only enables the electrode to be applied to any cell topology, by also is much easier to construct.

SUMMARY OF THE INVENTION AND ADVANTAGES

According to the present invention, there is provided a method and apparatus (20) for introducing molecules and macromolecules into a membrane vesicle, a cell or tissue by (a) applying a train of unipolar or alternating low voltage pulses to molecules/macromolecules and cells, (b) increasing the concentration of molecules/macromolecules at the surface of the cells, leading to an increased interaction of the molecules/macromolecules with the membrane of the cells while also causing electrophoretic movement of charged proteins and lipids in the cell membrane, and (c) causing the destabilization of the cell membrane whereby the molecules/macromolecules penetrate into the cytosol via an endocytic process and via diffusion through structural defects in the membrane lipid bilayer.

The present invention allows the introduction of molecules into cells and is not limited by the molecular weight of the molecules. There is a very high efficiency of incorporation of the molecules, including macromolecules, resulting in cytoplasmic concentrations that are at least an order of magnitude higher than the extracellular concentration of the molecule and macromolecules. The present invention also has a high survival rate of the treated cells. The method utilizes similar electrical parameters for the incorporation of molecules, including macromolecules, into different cell types. This permits ease of use of the invention.

The present invention also includes an apparatus (20) which includes a support plate (36) having apertures (38) for allowing electrodes (22) to pass therethrough. Support tubes (34) located within the apertures (38) slideably surround the electrodes (22). Electric current supplying means (32) connected to the electrodes (22) supplies sufficient electrical current to a cell for facilitating the introduction of molecules or macromolecules into the cell.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1A:
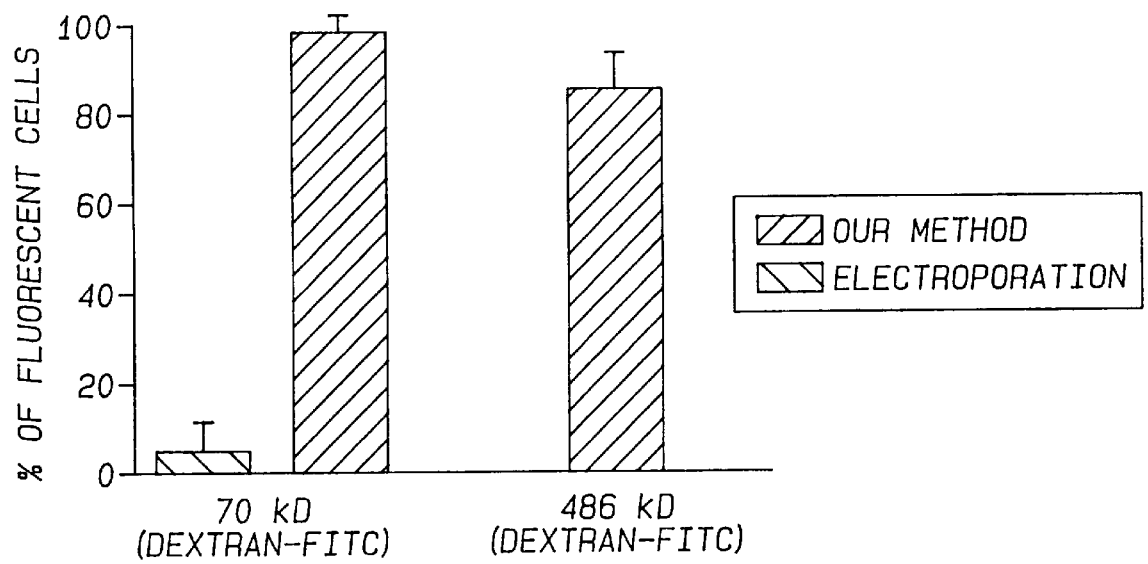
FIG. 1A is a bar graph comparing incorporation of 70 kD (Dextran-FITC) and 486 kD (Dextran-FITC) intracellularly into lymphocytes (Lymphoma B cells, I29) by electroporation (horizontal cross-hatching) as compared to the method of the present invention (diagonal cross-hatching), indicating the percentage of fluorescent cells, the electroporation being carried out by expressing the suspension to ten pulses of 1600 V/cm, 200 $\mu$sec duration of each pulse.

Generally, the present invention provides a method and apparatus for the introduction of molecules, including macromolecules, into a cell. The method is accomplished by the general steps of preparing either a suspension or an adherent growth of the cells and molecules to be introduced into the cells, and applying a train of unipolar or alternating low voltage pulses to the suspension or adherent layer to increase the concentration of the molecules at the cell surface. This leads to an increased interaction of the molecules/macromolecules with the lipid bilayer of the cell membranes driven by electric and thermal forces. At the same time, the unipolar or alternating train or series of trains of voltage pulses leads to electrophoretic movement of the charged proteins in the cell membranes causing their accumulation in one half of the cell. The accumulation of molecules/macromolecules at the cell surface and the electric and thermal forces acting on the macromolecules lead to an increased interaction of the macromolecules and molecules with the cell surface leading to a destabilization of the cell membrane. Cell membrane destabilization causes penetration of molecules and macromolecules into the cytosolic compartment of the cell via endocytic process which leads to increased vesicle formation with the molecules and macromolecules, are trapped inside the vesicles and/or the macromolecules penetrate the cells via diffusion through the induced structural defects in the lipid bilayer.

More specifically, a series of pulses, such as a single train or multiple trains of unipolar low-voltage direct current (D.C.) or alternating current (A.C.) pulses, is applied to an environment containing the cells and molecules. The term series is used to designate a single train of voltage pulses or a number of continuous repetitions of the train of voltage pulses or a number of continuous repetitions of the train of voltage pulses. These voltage pulses can be either unipolar or bipolar. This step of the process is a critical difference from other processes, such as electroporation.

In vitro, for cells growing in suspension, the cells are suspended in a medium of low conductance in order to limit electric heating effects and/or electrolytic reactions at the electrode—medium interface. Such medium may consist of 300 mM sucrose or mannitol in the presence of a small amount of a buffer (e.g. 1 to 3 mM Hepes) of a pK in the pH range of 7.0 to 8.0. In some cases, 5% glycerol can be added to the medium in order to enhance incorporation. Following the exposure to the electric field, the cells should be washed with PBS or growth medium and finally replacing the medium with fresh growth medium in the presence of 5%–10% FCS (fetal calf serum) or bovine calf serum. The train or series of trains of unipolar voltage pulses is applied by the application of two electrodes to the suspension. The electrodes could be made from different metal with the preference of using inert and non-polarizable electrodes (e.g., platinum or Ag/AgCl electrodes, correspondingly).

In vitro, for cells growing while attached or adhered to a surface such as a petri dish or culture flask, the cells are adhered to a surface by growth in a suitable growth medium as shown in FIGS. 9A–D, 10A–D, and 11A–D. The growth medium is then removed and replaced with a suitable incubation medium such as BGJ media supplemented with 10% FCS. An alternating current field (60 V/cm at 30 kHz) is then applied to the cells. Following exposure to the field, the cells are washed with PBS or medium and finally replaced with fresh growth medium. Unlike the treatment of suspended cells, the incorporation of macromolecules can be carried out in the presence of a very conductive medium. That is, macromolecules can be incorporated into cells in the presence of a highly conductive medium.

The present invention can also be applied to enhance incorporation of molecules into adherent cells by utilizing both the method and apparatus of the present invention. For use with adherent cells, there is no need to change the growth medium of the cells to a low conductivity medium. That is, the same medium used for cell growth can be utilized for reaction incorporating the macromolecule. The present invention can also be utilized in vivo by application of the molecules to be introduced at the site or area containing the cells which are the target of the introduction. Sites such as skin and internal tissues can be targets either invasively or non-invasively.

Figure 5:
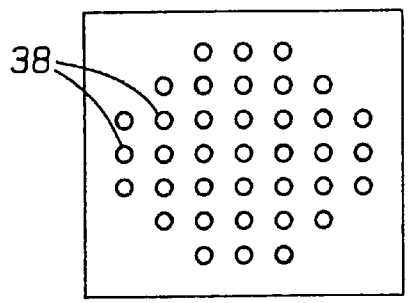
FIG. 5 is a top view of a main support plate of the present invention.
Figure 6:
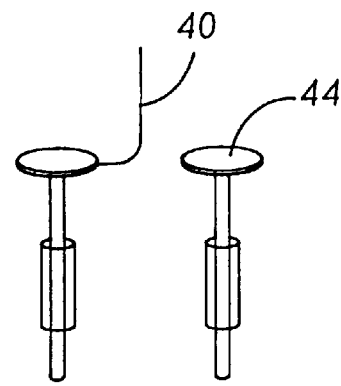
FIG. 6 is a side view of the electrodes of the present invention.

The apparatus of the present invention, generally shown at 20 in FIG. 3, is a new electrode type comprising a series of small needles 22 which are applied perpendicularly to a base 26 (plan) of a petri dish 24 containing an adherent cell layer (not shown). A lower end 28 of each needle 22, touches the base 26 of the dish 24 penetrating the cell monolayer while an upper end 30 of the needle 22 is connected to a pulse generator 32. The needles 22 are placed inside parallel tubes 34 and are held in arrangement by a support plate 36. The needles 22 can move freely within the tubes 34 so as to accommodate any cellular topology. That is, the needle electrodes 22 can move freely in the perpendicular direction to the plane of the cell or tissue layer. If the support plate 36 is thick enough, holes 38, as shown in FIG. 5, in the plate 36 can replace the tubes 34.

The needle electrodes 22 of the present invention can be constructed of any suitable conductive material such as stainless steel, platinum, and other metals or alloys of metals. The needle electrode 22 can also be covered with materials such as plastic in order to reduce the conductivity of the electrode or to change the direction of the field which is generated. Additionally, the needle electrodes 22 can be easily changed and discarded allowing for new needle electrodes 22 to be inserted thereby making the apparatus suitable for uses requiring sterility and patient contact.

The support plate 36 can be constructed of any suitable material, such as a plastic material.

Connection to the pulse generator (P.G.) 32 can be made in two different ways. The first alternative, as shown in FIGS. 4A–B, 6, and 8A, can be where the needles 22 are connected directly to the P.G. 32 by a very thin and properly insulated wires 40 in such a manner as to not to limit the free movement of the needles 22 inside the tube 34 or channel 38 in the main support plate 36. The insulation on the wire 40 avoids possible short circuiting of the needles 22.

Figure 3A:
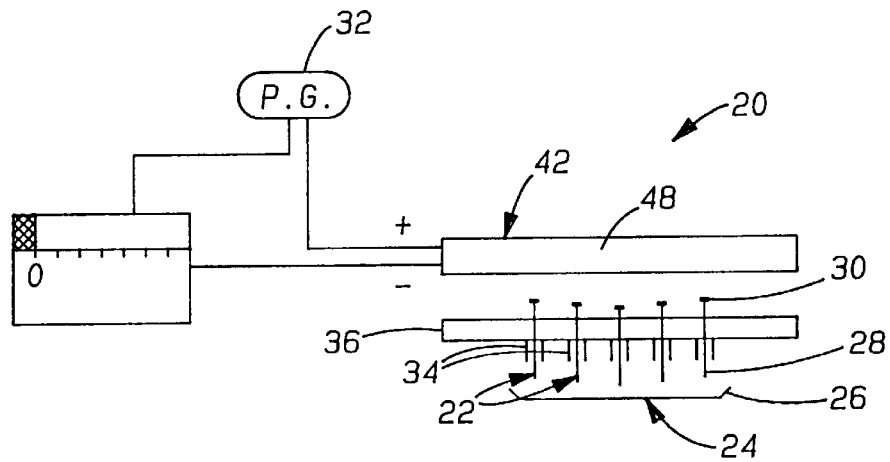
FIG. 3A is side view of the apparatus of the present invention showing electrodes in a disengaged position.
Figure 3B:
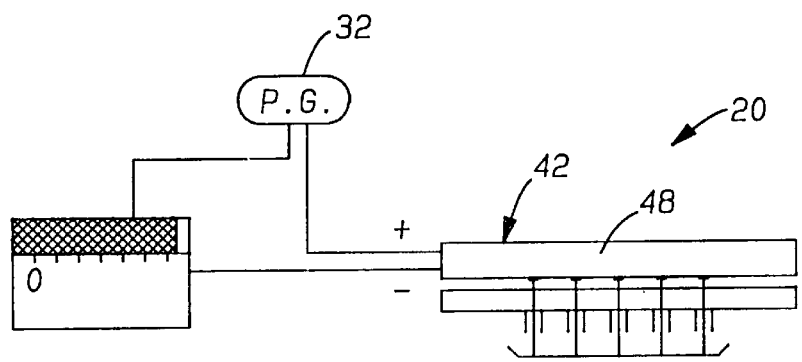
FIG. 3B is a side view of the apparatus of the present invention showing the electrodes in an engaged position.
Figure 4A:
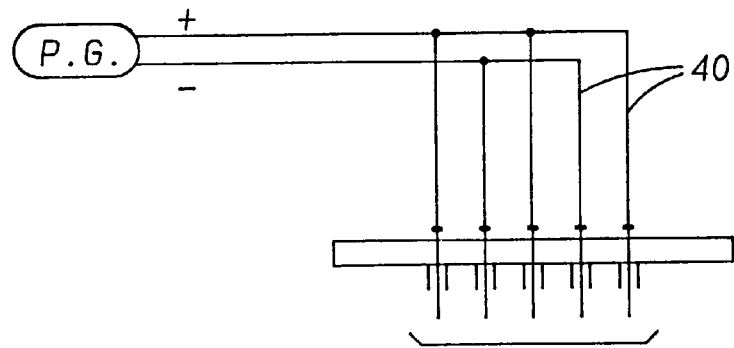
FIG. 4A is a schematic diagram illustrating connection of a pulse generator to the electrodes in the disengaged position.
Figure 4B:
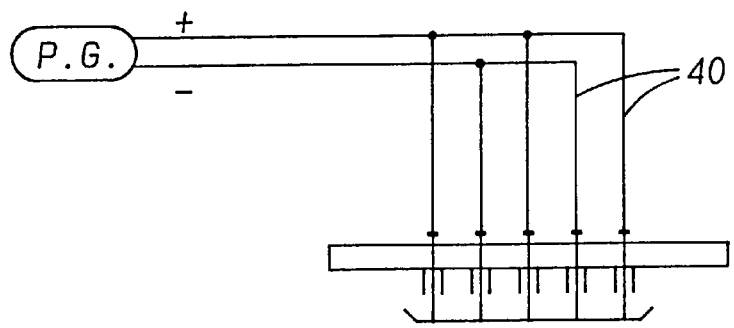
FIG. 4B is a schematic diagram illustrating the connection of the pulse generator to the electrodes in an engaged position.
Figure 8A:
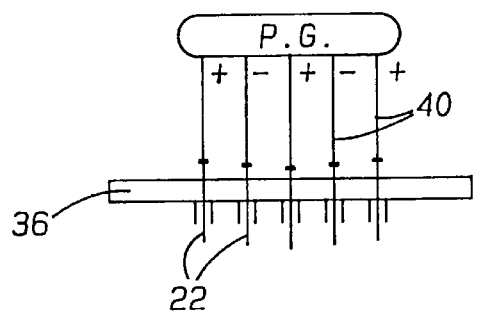
FIG. 8A is a diagram illustrating an embodiment of the present invention in which a direct current is applied to the electrodes.
Figure 8B:
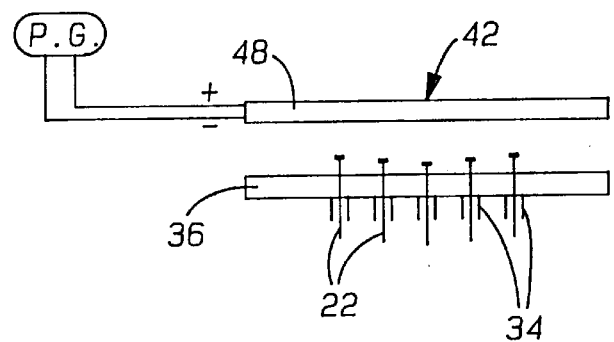
FIG. 8B is a diagram illustrating an embodiment of the present invention in which an alternating current is applied to the electrodes through a conductive plate.
Figure 9A:
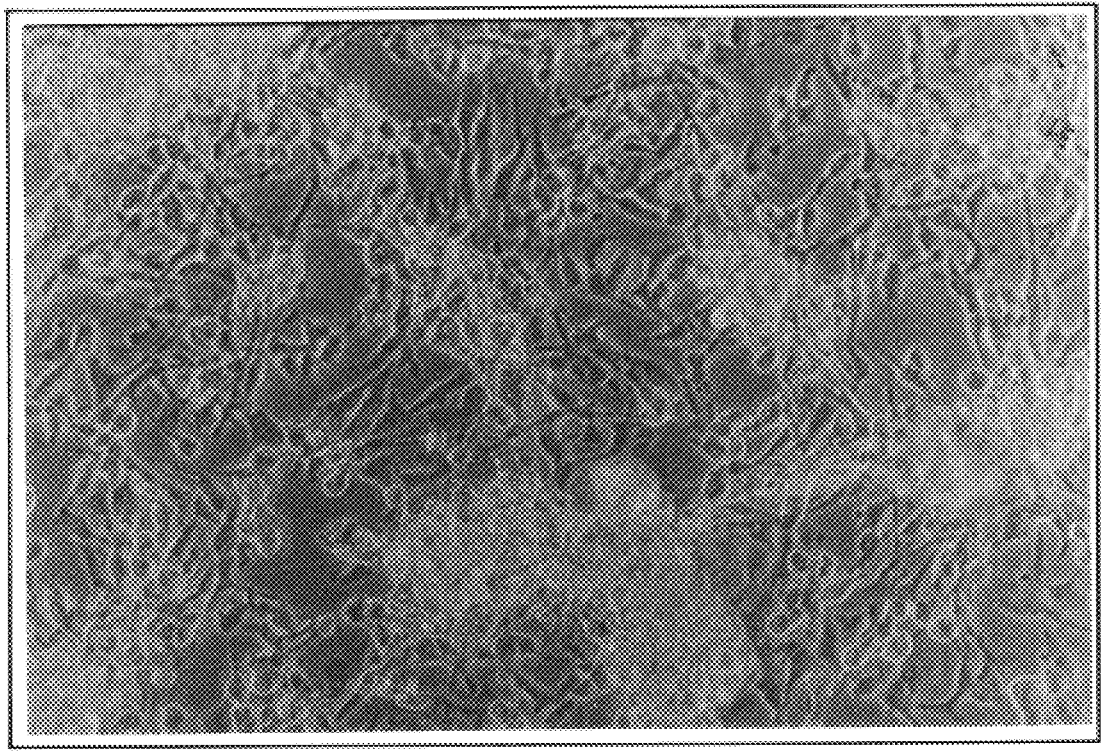
FIGS. 9A–D are photographs showing the intercellular incorporation of molecules of 150 kD Dextran-FITC by the present method into Lewis lung carcinoma cells adherently growing in petri dishes, wherein the cells were incubated in a low conductive medium composed of 0.3 M Manitol, 1.5 mM Hepes, pH=7.4. 20 mM 150 kD Dextran-FITC was added to the medium and where (A) Control (Phase microscope), (B) Control (fluorescent microscope), (C) Exposed ten minutes to a stimulus (D.C.) of 100 V/cm, 0.9 mSec, 1000 Hz (Phase microscope), (D) Exposed ten minutes to a stimulus (D.C.) of 100 V/cm, 0.9 mSec, 1000 Hz (fluorescent microscope) and the red fluorescence is produced by propidium iodide which was added to both samples in order to determine the proportion of dead cells.
Figure 9B:
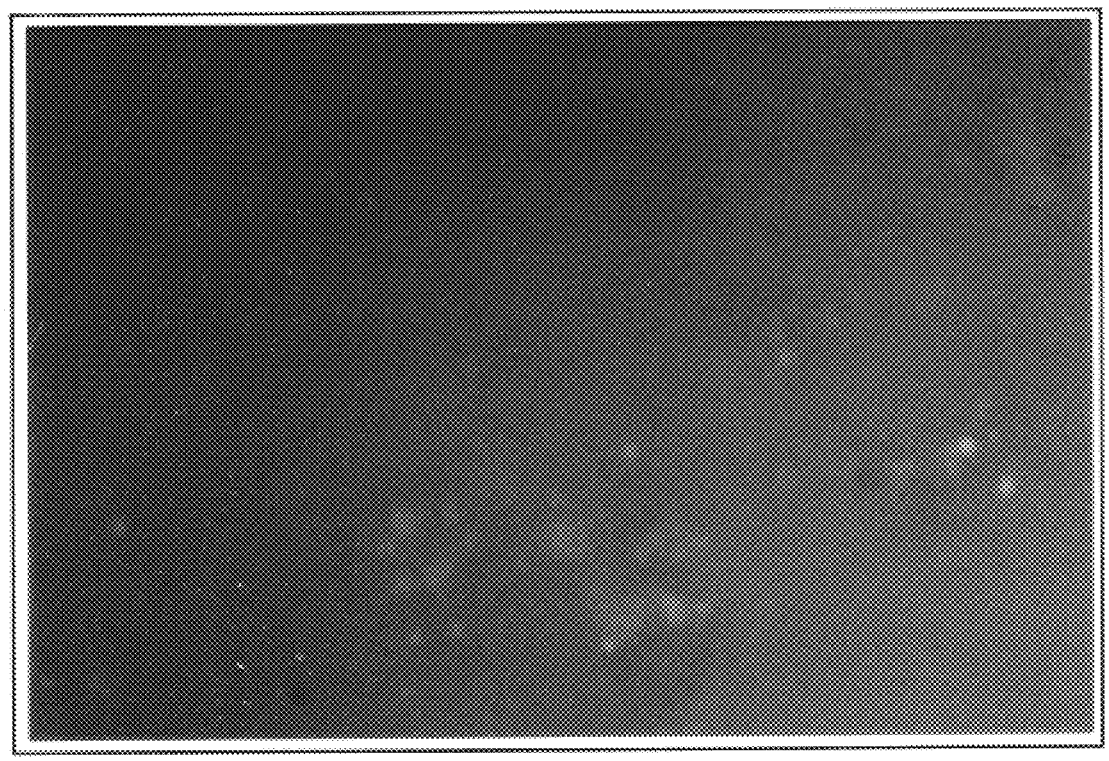
Figure 9C:
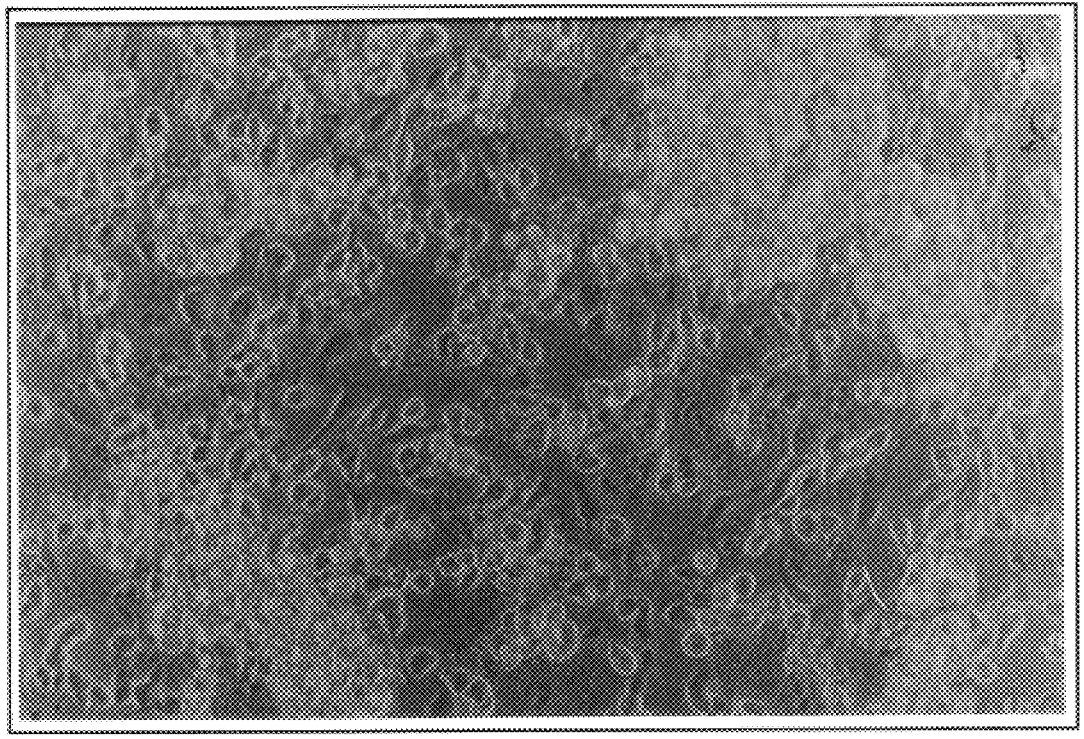
Figure 9D:
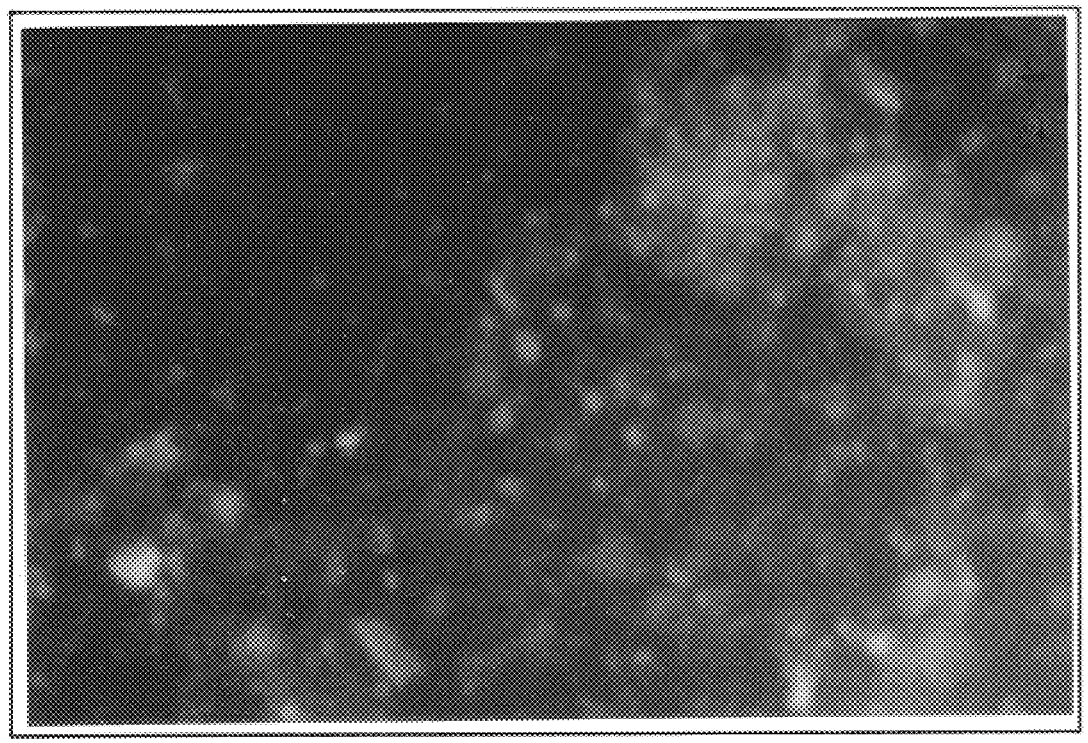
Figure 10A:
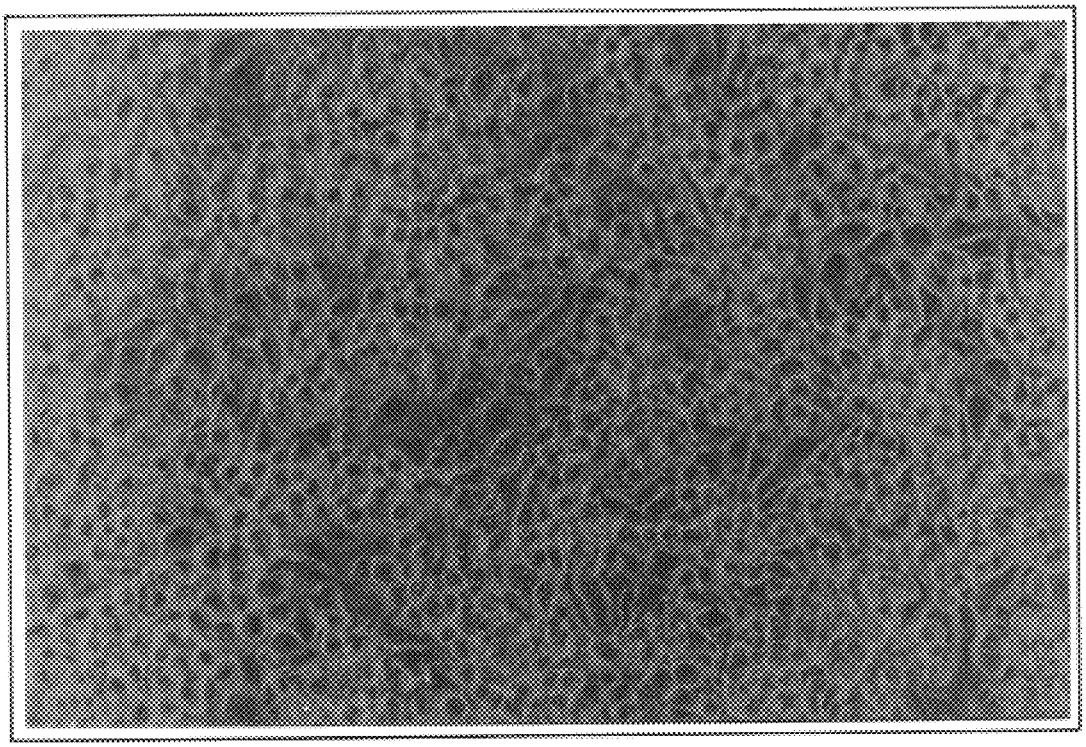
FIGS. 10A–D are photographs showing the intracellular incorporation of molecules of 2000 kD Dextran-FITC by the present method into Lewis lung carcinoma cells adherently growing in petri dishes, wherein a medium comprising BGJ+10% FCS into which 0.194 mM of 2000 kD Dextran-FITC was added and wherein (A) Control (Phase microscope), (B) Control (fluorescent microscope), (C) Exposed forty minutes to a stimulus (D.C.) of 90 V/cm, 0.9 mSec, 1000 Hz (Phase microscope) and (D) Exposed forty minutes to a stimulus (D.C.) of 90 V/cm, 0.9 mSec, 1000 Hz (fluorescent microscope)
Figure 10B:
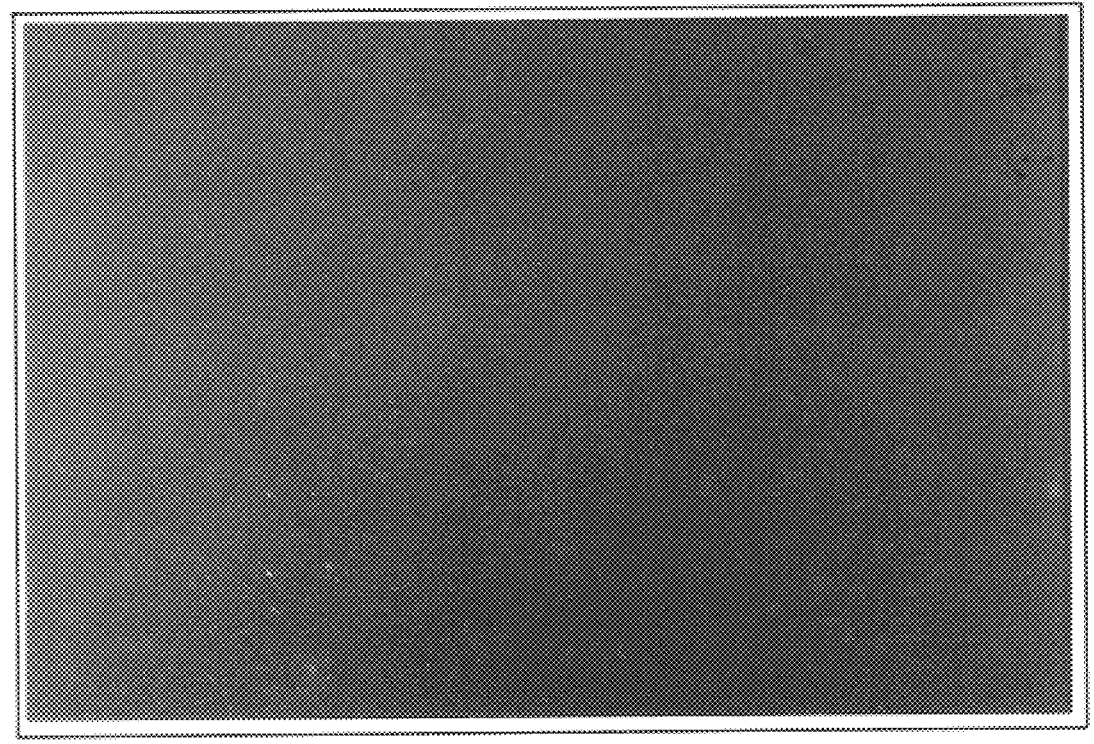
Figure 10C:
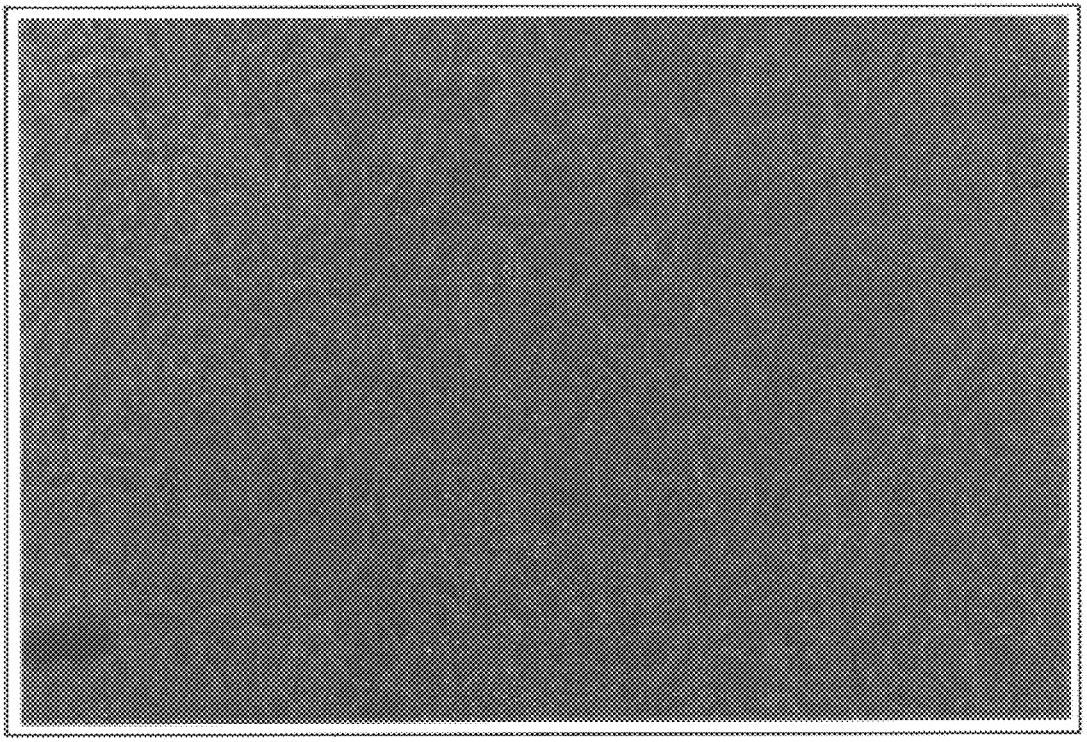
Figure 10D:
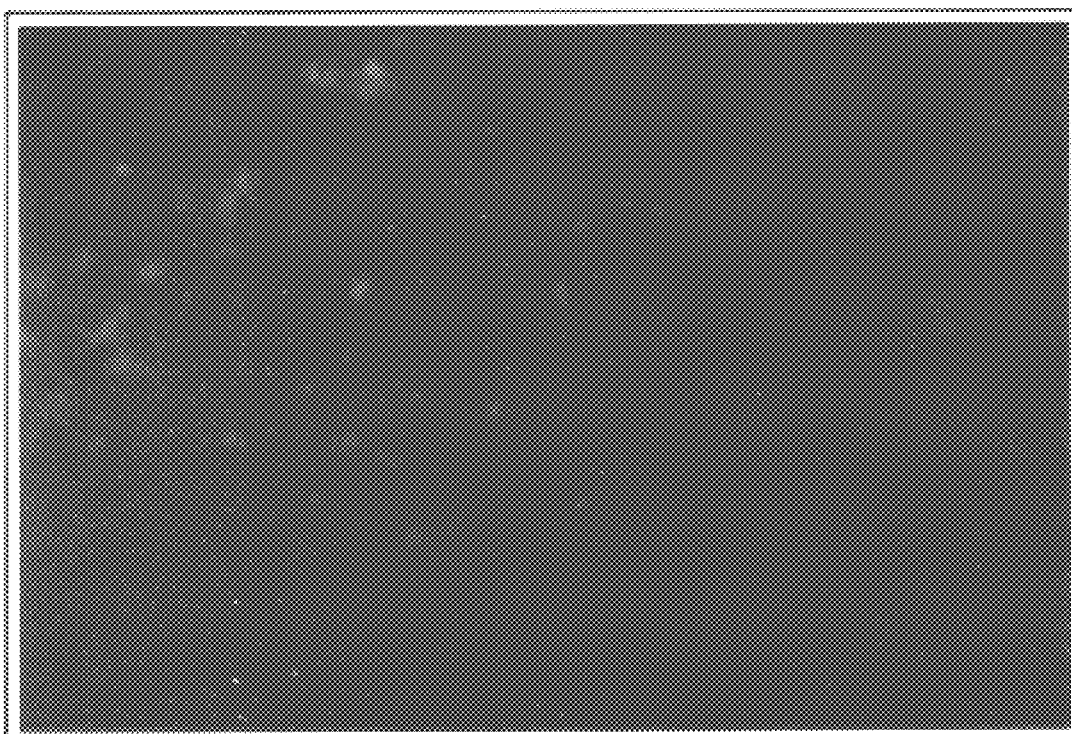
Figure 11A:
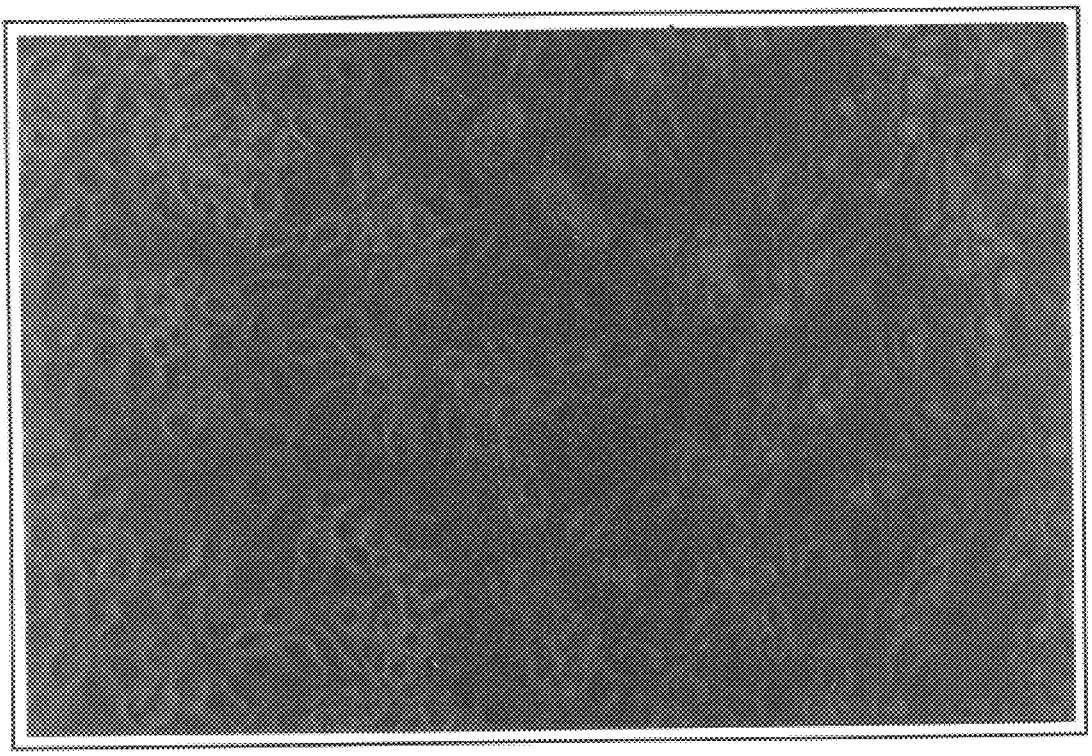
FIGS. 11A–D are photographs showing the intracellular incorporation of molecules of 70 kD Dextran-FITC Lewis lung carcinoma cells adherently growing in petri dishes, wherein the train of unipolar pulses was replaced by an A.C. stimulus and the medium of the reaction was BGJ+10% FCS to which 20 mM of 70 kD Dextran-FITC was added and wherein (A) Control (Phase microscope), (B) Control (fluorescent microscope), (C) Exposed fifty minutes to a stimulus (A.C.) of 60 V/cm, 30 kHz (Phase microscope), (D) Exposed fifty minutes to a stimulus (A.C.) of 60 V/cm, 30 kHz (fluorescent microscope).
Figure 11B:
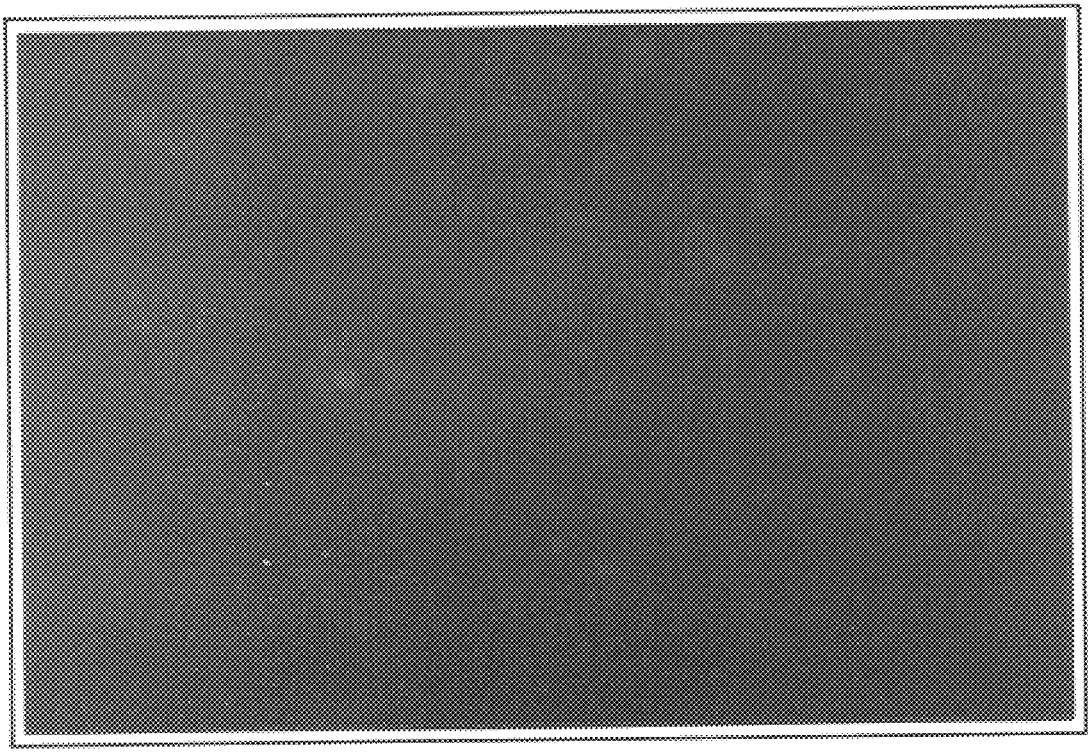
Figure 11C:
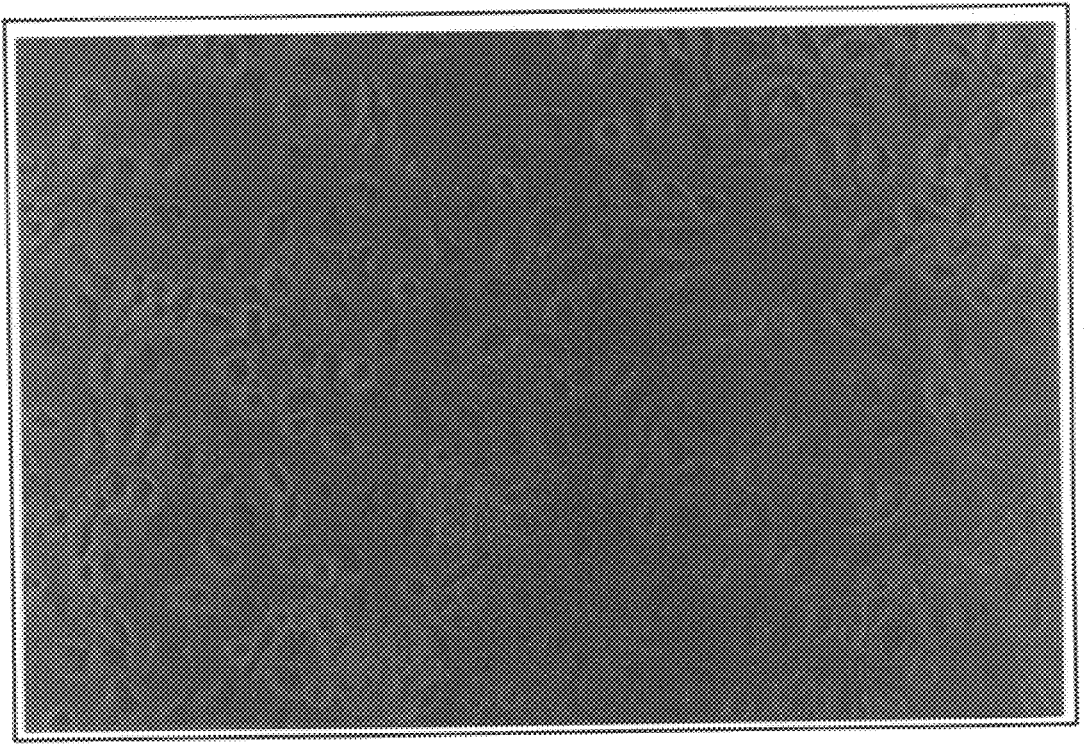
Figure 11D:
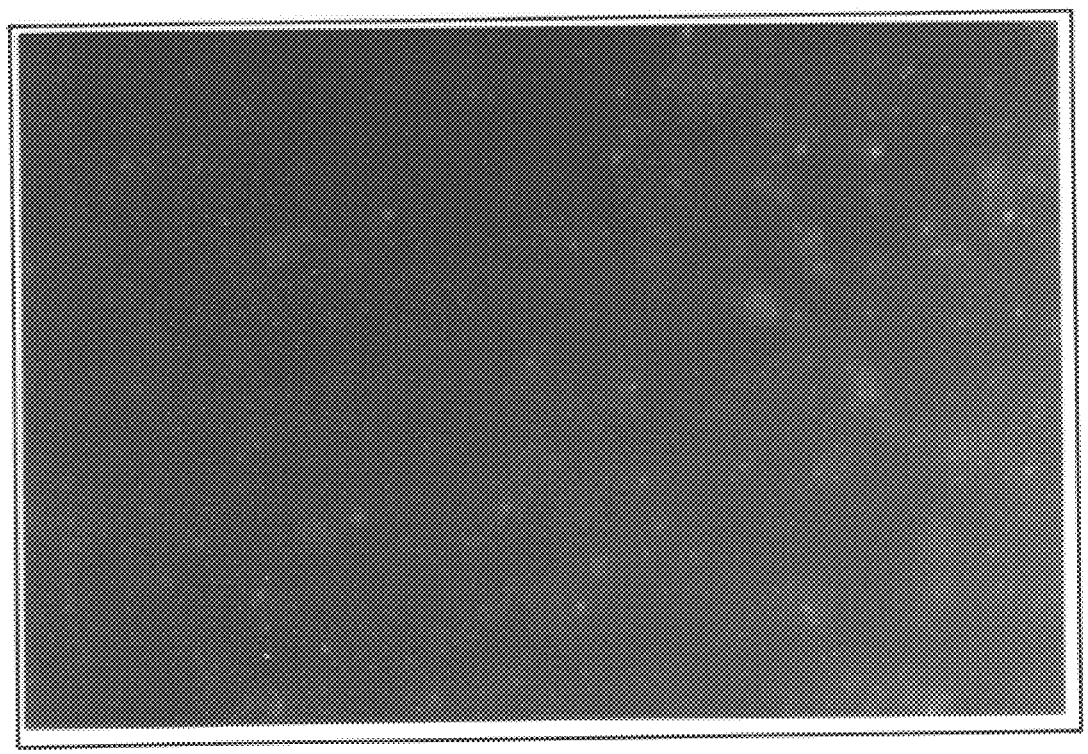

Referring to FIGS. 3A and 8B, a second alternative is shown wherein the P.G. 32 can be connected to a conductive plate 42 which is divided into single or conductive arrays 46 filled with a conductive gel (not shown). Contact of a head 44 of the needle 22 with the conductive gel connects the needles 22 with the P.G. 32. The conductive gel can comprise any suitable conductive material such as a mixture of 1 M KCl with 2% agarose.

Figure 7:
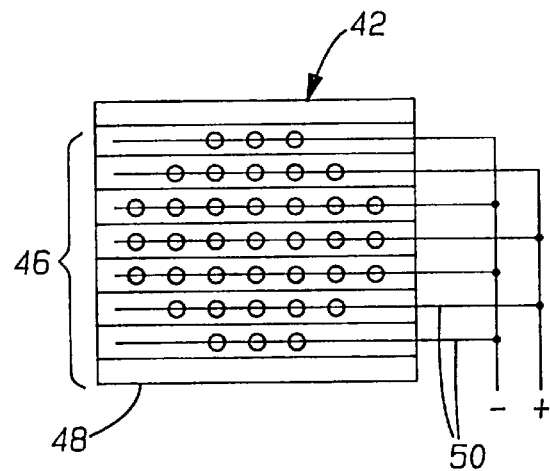
FIG. 7 is a top view of a conductive plate of the present invention connected to the pulse generator.

As shown in FIG. 7, the conductive array 46 of the conductive plate 42 includes a plate 48 which apertures 52 which contain the conductive gel which acts to connect leads or wires 50 which connect the conductive plate 42 to the power source P.G. 32. The apertures 52 placed in the conductive plate 42 also allow for selection or changes in the location of the electrodes 22 in order to obtain a desired electric field. In other words, the arrangement of the apertures 52 in the conductive plate 42 allows the user to configure the location of the electrodes 22 in order to either achieve a particular electric field among the cells or to configure the electrodes 22 such that the electrode 22 arrangement accommodates a particular space such as the circular conformation of a typical Petri dish 24. Additionally, the apparatus (20) does not require electrode contact with the cells in order to facilitate the incorporation molecules into the cell. The apparatus (20) creates electric field which facilitate the uptake of molecules without electrode-cell contact.

In operation, the electrode apparatus 20 can function in the following way: when the plate is pushed down towards the petri dish from a disengaged position (FIG. 3A) where the electrodes 22 are elevated above the surface of the cell layer toward an engaged position (FIG. 3B) where the electrodes 22 contact the cell layer and the needles electrodes 22 touch the bottom of the dish 26. Since the needle electrodes 22 are free to move inside the tubes 34, the head 44 of the needle electrode 22 moves upward with relation to the main support plate 36. Thus, when the heads 44 of the needle electrodes 22 move upward, it insures that the lower ends 28 of the needle electrodes 22 come into contact with the bottom 26 of the petri dish 24.

In the embodiment in which the P.G. 32 is connected through the conductive plate 42, the upper ends 30 of the needle electrodes 22 come into contact with the conductive gel as they move upward since the conductive plate 42 is closely positioned and parallel to the main support plate 36.

As illustrated in FIGS. 8A–B, the apparatus 20 of the present invention can be constructed so as to function with either a direct current (D.C.) source (FIG. 8A) or as with an alternating current (A.C.) source (FIG. 8B).

The effect of the present invention can be further effectuated by crosslinking the compounds to hydrophilic compounds (as carriers), such as bovine serum albumin. That is, the molecules can be found to be attached (covalently and noncovalently) to hydrophilic-charged carriers which potentiate the movement of the molecules as the pulses are applied, whereby increasing the efficiency of the system. The cellular effect involving the hydrophilic outer surface of the membrane combined with the effect of the train or series of trains of voltage pulses enable the concentration of the molecules and macromolecules at the cell surface. When the concentrated molecules at the cell surface collide with the cell membrane, the molecules aggregate at and into the hydrophilic portion of the membrane. Intracellular pinocytes are formed leading to increasing vesicle formation intracellularly. Thus, the molecules have achieved intracellular access. However, unlike other methods, the concentrating effect of the present invention results in an efficient concentrated introduction of the molecules into the cells. The vesicles formed contain a high concentration of the molecules, thereby creating an effectively efficient introduction of the molecules into the cell.

Alternatively, the same endpoint, loading or transfection, can be achieved by inducing the movement of cells towards non-charged molecules or macromolecules.

Molecules capable of incorporation by the present invention can be defined over a wide range. That is, the present invention enables an efficient introduction of molecules and macromolecules into living cells in vitro and in vivo. These molecules are within an extremely wide range of molecular weight. The molecules can range from the size of ions and small molecules up to proteins, antibodies, and large enzymes. Moreover, transfection with different DNA vectors may be possible by use of the present inventive method either by itself or in combination with other methods of transfection thereby enhancing the effectiveness of those methods. Other existing methods of incorporation include incorporation of macromolecules based on the use of chemical compounds e.g., DNA transfections based on the use of calcium phosphate precipitation.

As stated above, the present invention is based on electric field induced relative movement of charged molecules, charged macromolecules, or charged liposomes toward cells (or the converse) using appropriate electric field parameters which yield an accumulation of the charged entities near the cell membrane. Unlike prior art methods, the present invention does not use either high voltages, such as electroporation, or frequencies which create summation of voltage pulses in a way where the effective pulse is a summation of several pulses, resulting in equilibrating molecules between the extracellular and intracellular compartments. This method differs from electroporation (or the equivalent terms) by the following features:

1. The electric parameters used by the present invention to efficiently incorporate molecules/macromolecules into cells induce a transmembrane potential difference across the cell membrane which is much lower than the known threshold of transmembrane potential difference which causes electroporation to take place.
2. Electroporation and consequent uptake, under specific electric field parameters, were shown to be proportional to the volume of the biological object (e.g. cell, bacteria etc) which is exposed to the electric field. Under the experimental conditions of the present invention, the uptake by the method of the present invention is independent on the volume of the exposed biological object and may be proportional to the surface area of the object.
3. Uptake is not limited by the electrochemical potential difference across the membrane concentration. Under conditions of electroporation, at most the same concentration of molecules/macromolecules in the cytosol and in the external medium can be achieved. Under experimental conditions, applicants have demonstrated up to two orders of magnitude increase of molecules/macromolecules concentration in the cytosol as compared with the concentration in the external medium.

More specifically, in order to achieve an increased incorporation of the molecules into cells, the cell suspension or the cells adhered to a surface in the presence of the molecular entity to be incorporated are exposed to an electric field produced by several trains of electrical pulses. The amplitude of the voltage in each train or series of trains of pulses is in the amplitude range of 1 V/cm to 250 V/cm. The frequency range of the pulses is from 1 Hz to 50 MHz possessing pulse widths of 20 ns to 20 ms in the case of unipolar pulses (D.C.) and 10–100 kHz for bipolar (A.C.) pulses. The exact field characteristics to be applied depends upon the charge and the molecular weight of the specific molecules to be incorporated.

The present invention has possible applications in various fields. The present invention can be used to load drugs into cells for slow drug release. In this application, the drugs are the molecules being transferred into the cells via the present invention. Other molecules, such as dyes and tracers, can be loaded into cells for imaging-based diagnosis. In-situ enzymology (loading agents for diagnostics) can be accomplished. Loading of antibodies for therapy or diagnostics can be carried out.

The present invention can be used for incorporating drugs into specific cell or tissue types, for example loading of drugs into tumor tissue for cancer therapy. Likewise, enzymes can be loaded into cells for specific purposes.

Another area for use of the present invention, as discussed above, is in the field of genetic engineering and gene therapy. The present invention can be used as a means of transfection, as well as tissue gene therapy.

The above list of utilities is only a sampling of the possibilities for which the present invention can be used. The list is intended to be exemplary and not exhaustive of the uses of the present invention.

The following examples illustrate the application of the present invention:

MATERIALS AND METHODS

In the following examples, the following general conditions were used; any modifications are included with the specific example. Cells were generally treated at a concentration of $1-4 \times 10^6$/ml. Prior to exposure to the electric field, the cells were washed twice with reaction medium. The exposure to the electric field was carried out in reaction medium at a temperature range of 2° C. to 38° C. The molecule to be incorporated was also in the reaction medium at a concentration as detailed in the following examples, but generally within the range of 0.5 $\mu$M to 0.1 mM. The molecule is in the medium during exposure to the external electric field. Sometimes it is placed in ice for a short period after exposure to the external electric field. Following exposure, the cells were washed twice with the reaction medium. For long-term experiments, the cells were washed twice, after exposure, with culture medium containing 10% fetal calf serum and then cultured.

Cell viability following exposure was determined by trypan blue exclusion or propidium iodide uptake. In general, 40 minutes following exposure there was no viability difference between treated and untreated cells based on trypan blue exclusion. Proliferation was determined by $^3$H-thymidine incorporation and also by cell counting. Following exposure, the lymphocytes were screened for their ability to continue producing antibodies after being exposed to lipopolysaccharide (LPS). Uptake of molecules was measured by fluorescence microscopy or by a biochemical assay.

In general, the electric fields to which the cells were exposed consisted of several trains of pulses. The amplitude of the voltage in each train of pulse is in the amplitude range of 10V/cm to 250V/cm. The frequency range of the pulses is from 1 Hz to 50 MHz possessing pulse widths of 20 ns to 20 ms. The exact field characteristics to be applied depends upon the charge and the molecular weight of the specific molecules to be incorporated and is provided in the examples. The choice of the applied electric field also depends upon the medium composition and viscosity.

EXAMPLE 1

Five cellular systems were successfully treated by the method of the present invention to introduce 70 kD dextran into the cells with the experimental parameters summarized in Table 1. Percent uptake of the molecule was measured by the number of fluorescent cells with the results presented in Table 2. In general, 80–100% of the cells showed uptake, i.e. fluorescence, of the dextran. The medium of the reaction is composed of 0.3 M mannitol or sucrose and 1 mM buffer Hepes —NaOH or Tris-HCl, PH 7.0–8.0. The conductivity of the final medium is very low (<200 $\mu$MHO), so that the cells are washed three times in this medium before the exposure to the electric fields. After the exposure, the cells can be exposed to a 5%–10% glycerol in the medium of the washes. After the reaction, the cells are washed three times with the medium used for the culture of this specific line of cells. (RPMI +10% fetal calf serum, DMEM +10 fetal calf serum, PBS, etc.)

TABLE 1

(uptake of 70 kD Dextran)

Red Blood Cells (RBC):

Concentration: 20 $\mu$M
Medium: 0.3 M mannitol 1 mM Hepes-NaOH
Amplitude of electric field: 100 V/cm
Duration of electric field: 90 $\mu$sec at 1,000 Hz
Frequency: 120–1,000 Hz - (pulse width 90 $\mu$sec)
Time of single exposure: 21 seconds
Total number of exposures: 1
B-Lymphocytes ($I_{29}$):

Concentration: 20 $\mu$M
Medium: 0.3M sucrose, 1.2 mM tris-HCl, pH 8.0
Amplitude of electric field: 150 and 200 V/cm
Duration of electric field: 0.9 milliseconds
Frequency: 120 Hz
Time of a single exposure: 21 seconds
Total number of exposures: 6
Time between exposures: 40 seconds
Cos 5–7:

Concentration: 20 $\mu$M
Medium: 0.3M mannitol, 1 mM Tris pH 8.0
Amplitude of electric field: 100 V/cm
Duration of electric field: 0.9 milliseconds
Frequency: 200 Hz
Time of exposure: 21 seconds
Number of exposures: 5
Time between exposures: 40 seconds TABLE 1-continued (uptake of 70 kD Dextran)

Swollen thylakoid vesicles:

Concentration: 20 $\mu$M
Medium: 1.2 mM tris-HCl, pH 8.0
Amplitude of electric field: 100 V/cm
Duration of electric field: 0.9 milliseconds
Frequency: 200 Hz
Time of exposure: 21 seconds
Number of exposures: 5
Time between exposures: 40 seconds
Red Blood Cell Ghosts (Low pH Ghosts):

Concentration: 20 $\mu$M
Medium: 0.3M sucrose, 1.2 mM tris-HCl, pH 8.0
Amplitude of electric field: 150 V/cm
Duration of electric field: 0.9 milliseconds
Frequency: 120 Hz
Time of exposure: 21 seconds
Number of exposures: 6
Time between exposures: 40 seconds

TABLE 2

| Cellular System | % Cellular Uptake |
|---|---|
| RBC | 80%–100% |
| Lymphocytes $I_{29}$ | 80% |
| Cos 5–7 | 80%–100% |
| Swollen thylakoids vesicles | 80% |
| RBC (Ghosts) | 80%–100% |

As shown in Table 2, the cells all were fluorescent indicating the uptake of the 70kD-FITC dextran. The results for the swollen thylakoid vesicles refers to the population of vesicles which can be easily visualized under the microscope (1–10 $\mu$M). This is due to the fact that the vesicles are extremely heterogeneous in size, and it is difficult to determine an exact number. Also, the thylakoid membrane has an intrinsic red fluorescence, while the dextran was an FITC conjugate. Therefore, to distinguish uptake from binding, the vesicles were osmotically shrunk so that the value/area ratio changed.

EXAMPLE 2

Eight cellular systems were treated by the method of the present invention to introduce 486 kD dextran into cells under the conditions detailed in Table 3. The treatment was successful in 80–100% of the cell population (Table 4).

TABLE 3

(uptake of 486 kD Dextran)

Red Blood Cells (RBC)

Concentration: 0.5 $\mu$M
Medium: 0.3M mannitol, 1 mM Hepes pH 7.0
Amplitude of electric field: 150 V/cm
Duration of a single electric field pulse: 90 $\mu$seconds
Frequency: 1,000 Hz
Total time of exposure: 10 minutes
Number of exposures: 1
Lewis Lung (LL) Carcinoma:

Concentration: 0.5 $\mu$M
Medium: 1 mM tris-HCl, pH 8.0
Amplitude of electric field: 100 V/cm

TABLE 3-continued (uptake of 486 kD Dextran)

Duration of electric field: 0.9 milliseconds
Frequency: 200 Hz
Time of exposure: 21 seconds
Number of exposures: 5
Time between exposures: 40 seconds
B-Lymphocytes ($I_{29}$):

Concentration: 0.5 μM
Medium: 0.3M sucrose, 1.2 mM tris-HCl, pH 8.0
Amplitude of electric field: 150 and 200 V/cm
Duration of electric field: 0.9 milliseconds
Frequency: 120 Hz
Time of exposure: 21 seconds
Number of exposures: 6
Time between exposures: 40 seconds
Cos 5–7:

Concentration: 20 μM
Medium: 0.3 M mannitol, 1 mM Tris pH 8.0,
    1 mM Hepes pH 7.4
Amplitude of electric field: 100 V/cm
Duration of electric field: 90 μseconds
Frequency: 1000 Hz
Time of exposure: 15 minutes
Number of exposures: 1
Swollen thylakoid vesicles:

Concentration: 0.5 μM
Medium: 1.2 mM tris-HCl, pH 8.0
Amplitude of electric field: 100 V/cm
Duration of electric field: 0.9 milliseconds
Frequency: 100 Hz
Time of exposure: 21 seconds
Number of exposures: 5
Time between exposures: 40 seconds
Red Blood Cell Ghosts (Low pH Ghosts):

Concentration: 20 μM
Medium: 0.3 M sucrose, 1.2 mM tris-HCl, pH 8.0
Amplitude of electric field: 150 V/cm
Duration of electric field: 0.9 milliseconds
Frequency: 120 Hz
Time of exposure: 21 seconds
Number of exposures: 6
Time between exposures: 40 seconds

TABLE 4

| Cellular System | % Cellular Uptake |
| --- | --- |
| RBC | 80%–100% |
| Lewis Lung Carcinoma | 80% |
| Lymphocytes $I_{29}$ | 80%–100% |
| Cos 5–7 | 80%–100% |
| Swollen thylakoids vesicles | 80% |
| RBC (Ghosts) | 80%–100% |

Figure 1B:
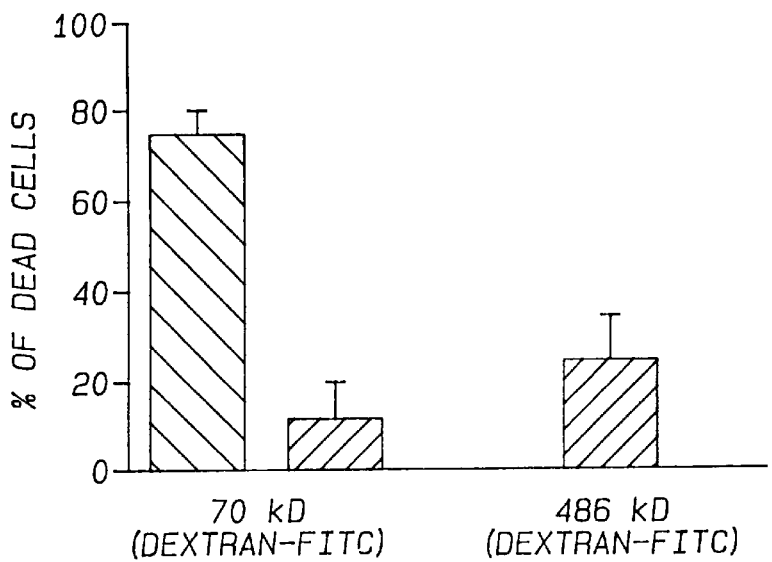
FIG. 1B is a bar graph comparing incorporation of 70 kD (Dextran-FITC) and 486 kD (Dextran-FITC) intracellularly into lymphocytes (Lymphoma B cells, I29) by electroporation (horizontal cross-hatching) as compared to the method of the present invention (diagonal cross-hatching)
Figure 2:
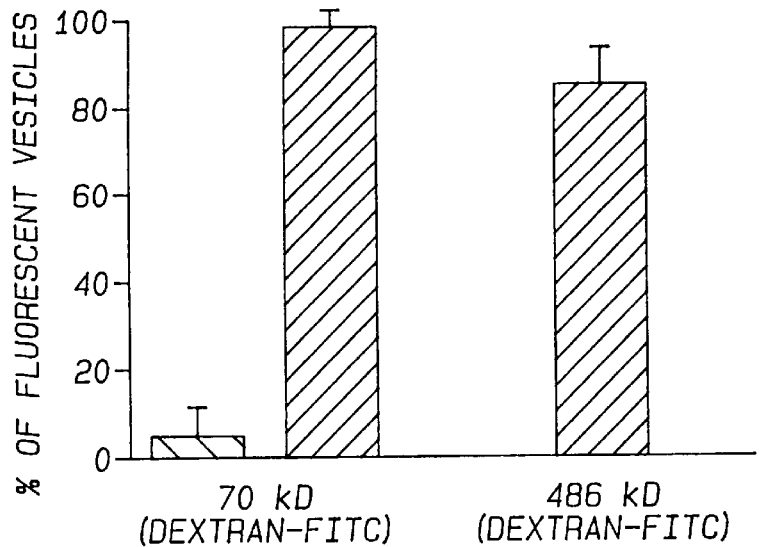
FIG. 2 is a bar graph showing the incorporation of 70 kD (Dextran-FITC) and 486 kD (Dextran-FITC) into membrane vesicles (thyllakoids) and comparing the present invention (diagonal cross-hatching) to the method of electroporation (horizontal cross-hatching)

These results can be compared to the results of utilizing electroporation to introduce 70 kD dextran into Lymphoma B cell, $I_{29}$ as shown in FIG. 1. Utilizing the lymphoma cells, electroporation resulted in approximately 80% dead cells and less than 5% showing any uptake of the 70 kD dextran. The method of the present invention resulted in less than 10% dead cells and greater than 90% uptake of 70 kD dextran. Similarly, utilizing membrane vesicles, as shown in FIG. 2, electroporation resulted in approximately 5% of the cells showing any uptake of 70 kD dextran. The method of the present invention resulted in greater than 90% uptake of 70 kD dextran.

EXAMPLE 3

β-Lymphocytes $I_{29}$ were successfully treated by the method of the present invention to introduce IgG-FITC into 85% of the cell population. The following parameters were used:

Concentration: 1 mg/ml
Medium: 1.0 mM tris-HCl, pH 8.0
Amplitude of electric field: 200 V/cm
Duration of electric field: 0.9 milliseconds
Frequency: 200 Hz
Time of exposure: 21 seconds
Number of exposures: 10
Time between exposures: 40 seconds

EXAMPLE 4

Utilizing the experimental parameters of Example 3, a specific antibody directed against tyrosine kinase and a non-specific antibody as a control were incorporated into the lymphoblasts. DNA synthesis ($^3$H-thymidine uptake) was measured at 48 hour post-incorporation. The synthesis of DNA was 2639 cpm as compared to the controls indicating 2411 cpm.

The loading of lymphocytes with an antibody against tyrosine phosphate (as compared to an unspecific antibody) resulted in a partial inhibition of antibody secretion from these cells. These results show a highly efficient introduction of antibodies into cells and a specific effect on the cellular machinery resulting from such an introduction. Tyrosine phosphate was chosen in order to check the involvement of tyrosine kinase with regard to the process of antibody production.

EXAMPLE 5

β-Galactosidase (540 kD) was introduced into Cos5–7 cells. The amount of enzyme incorporated into the cells was obtained a calorimetric assay using o-nitrophenyl-β-d-galactopyranoside as a substrate. The activity was calculated by subtracting the background activity (control sample) and dividing by the number of cells. The β-galactosidase was successfully inserted into the cells. The parameters used for incorporation were as follows:

Concentration: 5 μg/ml
Medium: 1 mM tris-HCl, pH 8.0, 6% glycerol
Amplitude of electric field: 100 V/cm
Duration of electric field: 90 μseconds
Frequency: 1000 Hz
Time of exposure: 21 seconds
Number of exposures: 5
Time between exposures: 40 seconds Since the concentration of the β-galactosidase was 5 μg/ml, the number of molecules of β-galactosidase per ml was $5.58 \times 10^{12}$ given that the volume of the cells was $2.7 \times 10^{-10}$. Therefore, the number of molecules recovered was $7.2 \times 10^4$. Theoretically, the number of molecules that could have been taken up if there was complete chemical equilibrium should have been no more than 1,496/cell. The number of molecules found per cell was 40 times larger than the theoretical calculation.

EXAMPLE 6

The above examples demonstrate that the problems associated with electroporation have been overcome by the present invention. It is a very efficient method (uptake by 80–1000% of the cell population) for loading molecules having molecular weights over an extended region of $1-10^4$ kD (Tables 1–3) including enzymes (e.g. β-galactosidase of 540 kD), antibodies (e.g. IgG of ≈160 kD) or plasmids (e.g. of 11.5 kD size). Moreover, a recovery of 80–90% viability of the cell population was obtained following the procedure of loading or transfection.

EXAMPLE 7

Incorporation of macromolecules by exposure to alternating current (AC) stimulus. The experiments were performed with the needle electrode system of the present invention. 3LL cells were adhered to petri dishes in the presence of growth medium. The medium was removed and replaced with incubation medium. The incubation medium consisted of growth medium (BGJ) supplemented with 10% FCS. To this medium was added Dextran-FITC molecules (70 kD) at a final concentration of 20 μM. A stimulating voltage having amplitude (peak to peak) 60 V/cm at a frequency of 30 kHz was applied for fifty minutes. Upon termination of the stimulus, the medium was removed. The petri dishes were washed six times with the same medium but without the Dextran-FITC 70 kD. The samples were then examined with a fluorescent microscope and photographed with 400 ASA film (Kodak) as shown in FIGS 11A–D.

EXAMPLE 8

Incorporation of Dextran-FITC (2000 kD) by unipolar voltage pulses. The experiment was performed with the needle electrode system of the present invention. 3LL cells formed a monolayer in petri dishes. The medium was removed and replaced by the incubation medium consisting of BGJ medium supplemented with 10% FCS. Then 2000 kD Dextran-FITC was added to a final concentration of 0.19 μM. The stimulating pulsed amplitude was 90 V/cm, the duration of the pulse was 0.9 mSec and the frequency was 1000 Hz. The stimulus was applied for forty minutes (one train of pulses). Finally, the stimulus was stopped and the medium was removed. The petri dishes were washed six times with the same medium but without Dextran-FITC 70 kD. The samples were examined with a fluorescent microscope and photographed with 400 Asa film (Kodak) as shown in FIGS. 10A–D.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

REFERENCES

Tatham and Lindau, (1990) *J. Gen. Physiol.* 95(3): 459–76.

We claim:

1. A method for introducing molecules and macromolecules into a membrane vesicle, cell or tissue by applying a train of unipolar or alternating voltage pulses having an amplitude of voltage in the range of 10V/cm to 150 V/cm at a frequency range of 1 Hz to 50 Mz, and at a pulse width of 20 ns to 20 ms to molecule/macromolecules and to at least one of said membrane vesicle, cell or tissue, and delivering the train of unipolar or alternating voltage pulses to the membrane vesicle, cell or tissue wherein the molecule/macromolecules are introduced therein.

2. A method of claim 1 further including the steps of preparing a suspension of and molecules/macromolecules to be introduced therein, and applying the train of voltage pulses to the suspension.

3. A method of claim 1 further including the steps of preparing an adherent growth of and molecules/macromolecules to be introduced therein, and applying the train of voltage pulses to the adherent cells.

4. A method of claim 1 further including the steps of introducing the molecules to an area of a population of cells in vivo and applying the train of voltage pulses to the area.

5. An electrode system (20) for use in introducing molecules and macromolecules into a membrane vesicle, cell or tissue, said electrode system (20) comprising: at least one independently movable needle electrode (22);

support plate means (36) having apertures (38) extending therethrough for supporting said electrodes (22) through said plate means (36); and electric current supply means (32) operatively connected to said electrodes (22) for supplying sufficient electrical current to a cell to facilitate the instruction of molecules or macromolecules into the cell, said electric current supply needs (32) further including a conductive plate filled with a conducted gel material, said conductive plate (42) conducting electric current through said electrodes (22) when said electrodes (22) contact said conductive plate (42).

\* \* \* \* \*

UNITED STATES PATENT AND TRADEMARK OFFICE
CERTIFICATE OF CORRECTION

PATENT NO. : 5,964,726
DATED : October 12, 1999
INVENTOR(S) : Korenstein et al.

Page 1 of 1

It is certified that error appears in the above-identified patent and that said Letters Patent is hereby corrected as shown below:

<u>Column 14,</u>
Line 16, change "1 Hz to 50 Mz," to read -- 1 Hz to 50 MHz, --

Signed and Sealed this

Thirtieth Day of April, 2002

Attest:

Attesting Officer

JAMES E. ROGAN
*Director of the United States Patent and Trademark Office*